(12) United States Patent
Ruan

(10) Patent No.: US 11,116,802 B2
(45) Date of Patent: *Sep. 14, 2021

(54) EXTRACT EFFECTIVE IN TREATING DRUG ADDICTION AND PREPARATION METHOD THEREFOR

(71) Applicant: GUANGXI JIUFU BIOTECHNOLOGY CO., LTD, Guangxi (CN)

(72) Inventor: Jun Ruan, Guangxi (CN)

(73) Assignee: GUANGXI JIUFU BIOTECHNOLOGY CO., LTD, Guangxi (CN)

( * ) Notice: Subject to any disclaimer, the term of this patent is extended or adjusted under 35 U.S.C. 154(b) by 53 days.

This patent is subject to a terminal disclaimer.

(21) Appl. No.: 16/258,688

(22) Filed: Jan. 28, 2019

(65) Prior Publication Data

US 2019/0151375 A1 May 23, 2019

Related U.S. Application Data

(63) Continuation of application No. PCT/CN2017/101679, filed on Sep. 14, 2017.

(30) Foreign Application Priority Data

Sep. 27, 2016 (CN) .......................... 201610860346.8

(51) Int. Cl.
| | | |
|---|---|---|
| A61K 35/618 | (2015.01) | |
| A61P 25/36 | (2006.01) | |
| A61K 31/575 | (2006.01) | |
| A23L 33/105 | (2016.01) | |
| A23L 33/10 | (2016.01) | |
| A23L 33/00 | (2016.01) | |
| C07D 493/08 | (2006.01) | |
| C07J 9/00 | (2006.01) | |

(52) U.S. Cl.
CPC ............ *A61K 35/618* (2013.01); *A23L 33/00* (2016.08); *A23L 33/10* (2016.08); *A23L 33/105* (2016.08); *A61K 31/575* (2013.01); *A61P 25/36* (2018.01); *C07D 493/08* (2013.01); *C07B 2200/13* (2013.01); *C07J 9/00* (2013.01); *Y02P 20/54* (2015.11)

(58) Field of Classification Search
None
See application file for complete search history.

(56) References Cited

U.S. PATENT DOCUMENTS

2006/0204601 A1 9/2006 Palu
2010/0209542 A1 8/2010 Boyer

FOREIGN PATENT DOCUMENTS

| CN | 1796400 | 7/2006 |
|---|---|---|
| CN | 102627682 | 8/2012 |
| CN | 102631371 A | 8/2012 |
| CN | 102697814 A | 10/2012 |
| CN | 103450310 | 12/2013 |
| CN | 103610699 A | 3/2014 |
| CN | 106146596 | 11/2016 |
| GN | 106800580 | 6/2017 |

OTHER PUBLICATIONS

Ning Zhu et al., "The Lipids of Slugs and Snails: Evolution, Diet and Biosynthesis", Dec. 29, 1994, pp. 869-875, vol. 29, No. 12, ACCS Press.
Jordi Folch et al., "A Simple Method for the Isolation and Purification of Total Lipides From Animal Tissues",1956, pp. 497-509, vol. 266, The Journal of Biological Chemistry.
Wang et al., "Pharmacological Study of Limax Extract on Inhibiting H14 Cell", Zhong Yao Cai, Jan. 2004, 27(1), pp. 33-35.
Hidayat Hussain et al., "Chemistry and biology of the genus *Voacanga*", Pharmaceutical Biology, Jul. 26, 2012, 50(9), 2012 Informa Healthcare USA, Inc., pp. 1183-1193.
M. D. Garcia et al., "Topical Antiinflammatory Activity of Phytosterols Isolated from Eryngium foetidum on Chronic and Acute Inflammation Models", Phytotherapy Research, 1999, 13(1), John Wiley & Sons, Ltd., pp. 78-80.
European Food Safety Authority, "Scientific Opinion on the safety of stigmasterol-rich plant sterols as food additive", EFSA Journal, 2012, 10(5), 2659, pp. 1-39.
T. Itoh et al., "Sterol Composition of 19 Vegetable Oils", Journal of the American Oil Chemists Society, Apr. 1973, vol. 50, pp. 122-125.
M. I. P. Kovacs et al., "A Simple Method for the Determination of Cholesterol and Some Plant Sterols in Fishery-Based Food Products", Journal of Food Science, 1979, 44(5), Institute of Food Technologists, pp. 1299-1301 & 1305.
Cai, "Study on the Optimum Extraction Process of Limax Polysaccharide", Dec. 15, 2008.
Chen, "The Pharmacological Research Process of Limax", Dec. 31, 2013.

(Continued)

*Primary Examiner* — Terry A McKelvey
*Assistant Examiner* — Catheryne Chen
(74) *Attorney, Agent, or Firm* — Winston Hsu

(57) ABSTRACT

Disclosed are an extract that is effective in treating drug addiction and a preparation method therefor. An effective component of the extract has the following chemical structural characteristics: a cholestenol compound with hydroxyl (OH) at position 3 and a double bond between position 5 and position 6, or a cholestenol compound with hydroxyl (OH) at position 3, a double bond between position 5 and position 6 and a double bond between position 22 and position 23. The extract can be extracted from the traditional Chinese medicine *Agriolima agrestis*. The extract of the present invention is safe in acute toxicity, sedative and hypnotic without physical and psychic dependence, has an inhibitory effect on excitability in mouse caused by morphine and benzedrine and a detoxification treatment effect on the withdrawal symptoms in morphine-dependent rats, and is useful in the development of medications or food for treating drug addiction.

3 Claims, No Drawings

(56) References Cited

OTHER PUBLICATIONS

Wang, "Screening the effective extraction of Limax against lung carcinoma and investigation of its activity", Dec. 31, 2014.
Xiang, "The Process Technology of Rice Bran", Apr. 30, 2014.
Liu, "The Traditional Chinese Medicine Resource of Jiangxi", Dec. 31, 2015.

EXTRACT EFFECTIVE IN TREATING DRUG ADDICTION AND PREPARATION METHOD THEREFOR

CROSS REFERENCE TO RELATED APPLICATIONS

This application is a continuation application of International Application No. PCT/CN2017/101679 filed on 2017 Sep. 14, which claims priority to China patent application CN201610860346.8. The contents of the above-mentioned application are all hereby incorporated by reference.

BACKGROUND OF THE INVENTION

1. Field of the Invention

The present invention relates to the technical field of biological medicines, and particularly to an extract that is effective in treating drug addiction and a preparation method therefor.

2. Description of the Prior Art

Drugs are narcotic and psychotropic drugs that can cause addiction, and cause serious harm to the body mechanism, physical and mental health of human and to the social environment. At present, there are more and more drug users, and the age is getting younger. The number of drug users in China alone is more than 14 millions, and the number of drug users worldwide is 200-400 millions. The types of drugs are becoming more diverse, and developed from opium and marijuana to heroin, Ketamine, and methamphetamine.

Drug rehabilitation and prohibition have always been a worldwide problem. So far, there is no good solution. The methods for treating drug addiction popular in the whole-world include compulsive treatment or an alternative therapy by treating the addict with another drug attack. Compulsive treatment is painful, arduous, and long time consuming. Alternative therapies with, for example, methadone and naltrexone replace one drug with another, or temporarily block opioid receptors, but they cannot enable the drug addicts to completely withdraw from the drugs physically and psychologically, and readdiction and relapse tend to occur. Just like the treatment of alcohol addiction with low-alcohol liquor in place of high-alcohol liquor, the highly addictive drugs are simply replaced with drugs that are slightly addictive in the alternative therapies.

For hundreds of years, attempts are made to find a safe and non-dependent medication for treating drug addiction, but all in vain. Therefore, it is of great significance to study a medication that is effective in treating drug addiction, and makes it difficult for the drug users to readdict and relapse.

SUMMARY OF THE INVENTION

An object of the present invention is to provide an extract that is effective in treating drug addiction and a preparation method therefor, to solve the problems that the existing method for treating drug addiction is not effective in detoxification, and readdiction and relapse tend to occur.

The following technical solution is adopted in the present invention.

An extract that is effective in treating drug addiction is provided, which mainly comprises a cholestenol compound with hydroxyl at position 3 and a double bond between position 5 and position 6, or a cholestenol compound with hydroxyl at position 3, a double bond between position 5 and position 6 and a double bond between position and position 23, having structural characteristics of

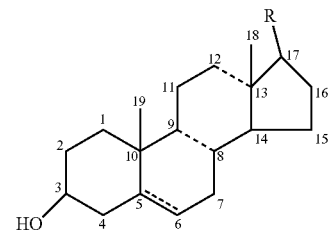

The extract is useful in the development of medications and foods for treating drug addiction, and can be prepared into drinks, tablets or capsules.

Preferably, the cholestenol compound includes brassicasterol having a structural characteristic of

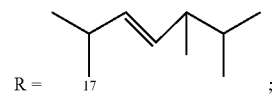

or stigmasterol having a structural characteristic of

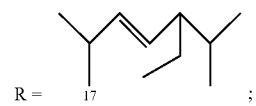

or β-sitosterol having a structural characteristic of

or cholesterol having a structural characteristic of

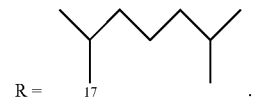

Preferably, the extract is extracted from the traditional Chinese medicine *Agriolima agrestis*, including one of *Limax maximus* L., *L. flavus* L., *Agriolimax agrestis* L., and *Phiolomycus bilineatus*.

The present invention also provides a method for preparing an extract that is effective in treating drug addiction, which comprises the following steps:

S1: removing impurities from the traditional Chinese medicine *Agriolima agrestis*, and smashing to 20 meshes for later use;

S2: feeding the traditional Chinese medicine *Agriolima agrestis* treated in Step S1 to a supercritical $CO_2$ extractor, and extracting for 4 hrs under a pressure of 25 KPa, at a temperature of 65° C. and a flow rate of 400-500 PV, to produce an extract for later use;

S3: adding the extract obtained in Step S2 to potassium hydroxide and deionized water, mixing uniformly according to a weight ratio of the extract: potassium hydroxide: deionized water 1:1:1.5, and heating with stirring to cause a saponification reaction, where the heating temperature is 85-100° C. and the reaction time is 2 hrs, to produce a reaction solution A that is allowed to stand and cool for later use;

S4: adding the reaction solution A obtained in Step S3 to ethyl acetate, and extracting (×4), where the amount of ethyl acetate added is three times the amount of the reaction solution A upon each extraction; washing the formed ethyl acetate solution layer with deionized water (×6-7), until the washing liquid is neutral (pH=7); separating the ethyl acetate solution, recovering ethyl acetate under reduced pressure, and concentrating to give a thick paste A for later use; and S5: adding the thick paste A obtained in Step S4 to methanol, where the amount of methanol is 5 times the amount of the thick paste A, dissolving by heating, filtering, standing and cooling for 48 h, crystallizing, filtering to obtain a crystal A, and drying the crystal A under reduced pressure at a temperature that is not more than 60° C., to obtain an extract that is effective in treating drug addiction.

The present invention also provides another method for preparing an extract that is effective in treating drug addiction, which comprises following steps:

Step 1: removing impurities from the traditional Chinese medicine *Agriolima agrestis*, and smashing to 20 meshes for later use;

Step 2: feeding the traditional Chinese medicine *Agriolima agrestis* treated in Step 1 to a multi-functional extractor; adding a solvent and extracting twice under reflux, where the first amount of the solvent added is 10 times the weight of the *Agriolima agrestis*, the time of extraction under reflux is 1.5 hrs, and an extract A is obtained after filtration; and the second amount of the solvent added is 8 times the weight of the *Agriolima agrestis*, the time of extraction under reflux is 1.0 hrs, and an extract B is obtained after filtration; combining the extract A and the extract B, and recovering the solvent under reduced pressure, to obtain a thick paste B for later use;

Step 3: adding the thick paste B obtained in Step 2 to potassium hydroxide and deionized water, mixing uniformly according to a weight ratio of the thick paste B: potassium hydroxide:deionized water 1:1:1.5, and heating with stirring to cause a saponification reaction, where the heating temperature is 85-100° C. and the reaction time is 2-4 h, to produce a reaction solution B that is allowed to stand and cool for later use;

Step 4: adding the reaction solution B obtained in Step 3 to ethyl acetate, and extracting (×4), where the amount of ethyl acetate added is three times the amount of the reaction solution B upon each extraction; washing the formed ethyl acetate solution layer with deionized water (×6-7), until the washing liquid is neutral (pH=7); separating the ethyl acetate solution, recovering ethyl acetate under reduced pressure, and concentrating to give a thick paste C for later use; and Step 5: adding the thick paste C obtained in Step 4 to methanol, where the amount of methanol is 5 times the amount of the thick paste C, dissolving by heating, filtering, standing and cooling for 48 hrs, crystallizing, filtering to obtain a crystal B, and drying the crystal B under reduced pressure at a temperature that is not more than 60° C., to obtain an extract that is effective in treating drug addiction.

Preferably, the solvent in Step 2 comprises one or two of n-hexane, ethanol, methanol, acetone, chloroform, an oil, gasoline, petroleum ether, diethyl ether and ethyl acetate.

The crystalline extract obtained by the above preparation method is further separated by preparative Middle-Pressure Liquid Chromatography (MPLC) under separation conditions including reverse C18 column (HT3501), solvent system: methanol:acetonitrile:isopropanol:water 70:20:6:4, and flow rate: 50 ml/min. Four main monomeric components are obtained, which are identified to be cholesterol, β-sitosterol, brassicasterol, and stigmasterol by nuclear magnetic resonance (NMR) spectrum.

The present invention has the following beneficial effects.

The extract that is effective in treating drug addiction prepared in the present invention is sedative and hypnotic without physical and psychic dependence, has an inhibitory effect on the excitability caused by morphine and benzedrine and a detoxification treatment effect on the withdrawal syndrome, and can achieve the purpose of physiological detoxification after 7 to 15 days of administration, without causing relapse.

These and other objectives of the present invention will no doubt become obvious to those of ordinary skill in the art after reading the following detailed description of the preferred embodiment that is illustrated in the various figures and drawings.

DETAILED DESCRIPTION

The present invention will be further described in detail below in conjunction with specific embodiments. It is to be understood that the following description is merely illustrative, and is not intended to limit the scope of the present invention.

EXAMPLE 1

An extract that is effective in treating drug addiction is provided, which mainly comprises a cholestenol compound with hydroxyl at position 3 and a double bond between position 5 and position 6, having structural characteristics of

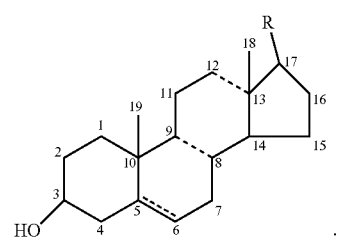

The cholestenol compound comprises β-sitosterol, having a structural characteristic of

or cholesterol structural characteristic of

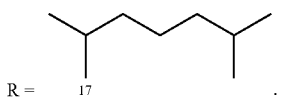

The extract can be extracted from traditional Chinese medicine *Agriolima agrestis*, including one of *Limax maximus* L., *L. flavus* L., *Agriolimax agrestis* L., and *Phiolomycus bilineatus*.

A method for preparing an extract that is effective in treating drug addiction is provided, which comprises following steps:

S1: removing impurities from the traditional Chinese medicine *Agriolima agrestis*, and smashing to 20 meshes for later use;

S2: weighing 60 kg of the traditional Chinese medicine *Agriolima agrestis* treated in Step S1, feeding to a supercritical $CO_2$ extractor, and extracting for 4 hrs under a pressure of 25 KPa, at a temperature of 65° C. and a flow rate of 400 PV, to produce 3.5 kg of an oily extract for later use;

S3: adding the extract obtained in Step S2 to potassium hydroxide and deionized water, mixing uniformly according to a weight ratio of the extract: potassium hydroxide: deionized water 1:1:1.5, that is, adding 3.5 kg of the extract, 3.5 kg of potassium hydroxide and 5.25 kg of deionized water to a reactor, and heating with stirring to cause a saponification reaction, where the heating temperature is 85° C. and the reaction time is 2 h, to produce a reaction solution that is allowed to stand and cool for later use;

S4: adding the reaction solution obtained in Step S3 to an extractor, adding ethyl acetate, and extracting (×4), where the amount of ethyl acetate added is 36.75 kg upon each extraction; washing the formed ethyl acetate solution layer with deionized water (×6), until the washing liquid is neutral (pH=7); separating the ethyl acetate solution, recovering ethyl acetate under reduced pressure, and concentrating to give 0.6 kg of a thick paste for later use; and S5: adding the thick paste obtained in Step S4 to 3.0 kg of methanol, dissolving by heating, filtering while hot, standing and cooling the filtrate for 48 h, crystallizing, filtering to obtain a crystal, and drying the crystal under reduced pressure at a temperature that is not more than 60° C., to obtain 267 g of an extract that is effective in treating drug addiction.

The extract is useful in the development of medications and foods for treating drug addiction, and can be prepared into drinks, tablets or capsules.

EXAMPLE 2

An extract that is effective in treating drug addiction is provided, which mainly comprises a cholestenol compound with hydroxyl (OH) at position 3, a double bond between position 5 and position 6 and a double bond between position 22 and position 23, having structural characteristics of

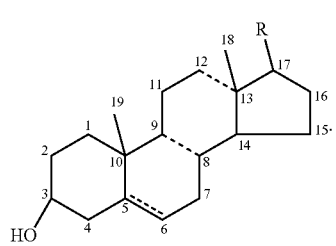

The cholestenol compound comprises brassicasterol, having a structural characteristic of

or stigmasterol, having a structural characteristic of

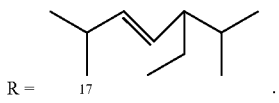

The extract can be extracted from traditional Chinese medicine *Agriolima agrestis*, including one of *Limax maximus* L., *L. flavus* L., *Agriolimax agrestis* L., and *Phiolomycus bilineatus*.

A method for preparing an extract that is effective in treating drug addiction is provided, which comprises following steps:

S1: removing impurities from the traditional Chinese medicine *Agriolima agrestis*, and smashing to 20 meshes for later use;

S2: weighing 60 kg of the traditional Chinese medicine *Agriolima agrestis* treated in Step S1, feeding to a supercritical $CO_2$ extractor, and extracting for 4 hrs under a pressure of 25 KPa, at a temperature of 65° C. and a flow rate of 500 PV, to produce 3.5 kg of an oily extract for later use;

S3: adding the extract obtained in Step S2 to potassium hydroxide and deionized water, mixing uniformly according to a weight ratio of the extract: potassium hydroxide: deionized water 1:1:1.5, that is, adding 3.5 kg of the extract, 3.5 kg of potassium hydroxide and 5.25 kg of deionized water to a reactor, and heating with stirring to cause a saponification reaction, where the heating temperature is 100° C. and the reaction time is 2 h, to produce a reaction solution that is allowed to stand and cool for later use;

S4: adding the reaction solution obtained in Step S3 to an extractor, adding ethyl acetate, and extracting (×4), where the amount of ethyl acetate added is 36.75 kg upon each extraction; washing the formed ethyl acetate solution layer with deionized water (×7), until the washing liquid is neutral (pH=7); separating the ethyl acetate solution, recovering ethyl acetate under reduced pressure, and concentrating to give 0.6 kg of a thick paste for later use; and S5: adding the thick paste obtained in Step S4 to 3.0 kg of methanol, dissolving by heating, filtering while hot, standing and cooling the filtrate for 48 h, crystallizing, filtering to obtain a crystal, and drying the crystal under reduced pressure at a temperature that is not more than 60° C., to obtain 267 g of an extract that is effective in treating drug addiction.

The extract is useful in the development of medications and foods for treating drug addiction, and can be prepared into drinks, tablets or capsules.

EXAMPLE 3

An extract that is effective in treating drug addiction is provided, which mainly comprises a cholestenol compound with hydroxyl at position 3 and a double bond between position 5 and position 6, having structural characteristics of

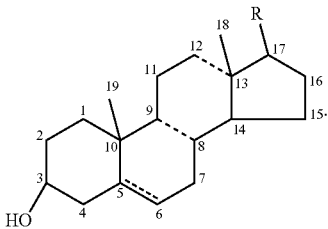

The cholestenol compound comprises β-sitosterol, having a structural characteristic of

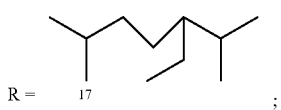

or cholesterol structural characteristic of

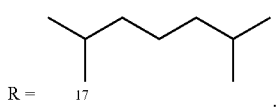

The extract can be extracted from traditional Chinese medicine *Agriolima agrestis*, including one of *Limax maximus* L., *L. flavus* L., *Agriolimax agrestis* L., and *Phiolomycus bilineatus*.

A method for preparing an extract that is effective in treating drug addiction is provided, which comprises following steps:

Step 1: removing impurities from the traditional Chinese medicine *Agriolima agrestis*, and smashing to 20 meshes for later use;

Step 2: weighing 100 kg of the traditional Chinese medicine *Agriolima agrestis* treated in Step 1, feeding to a multi-functional extractor; adding a solvent and extracting twice under reflux, where the first amount of the solvent added is 1000 kg, the time of extraction under reflux is 1.5 hrs, and an extract A is obtained after filtration; and the second amount of the solvent added is 800 kg, the time of extraction under reflux is 1.0 hrs, and an extract B is obtained after filtration; combining the extract A and the extract B, and recovering the solvent under reduced pressure, to obtain 8.1 kg of a thick paste A for later use;

Step 3: adding the thick paste A obtained in Step 2 to potassium hydroxide and deionized water, mixing uniformly according to a weight ratio of the thick paste A: potassium hydroxide:deionized water 1:1:1.5, that is, adding 8.1 kg of the thick paste A, 8.1 kg of potassium hydroxide and 12.2 kg of deionized water to a reactor, and heating with stirring to cause a saponification reaction, where the heating temperature is 85° C. and the reaction time is 2 h, to produce a reaction solution that is allowed to stand and cool for later use;

Step 4: adding the reaction solution obtained in Step 3 to an extractor, adding ethyl acetate, and extracting (×4), where the amount of ethyl acetate added is 85.2 kg upon each extraction; washing the formed ethyl acetate solution layer with deionized water (×6), until the washing liquid is neutral (pH=7); separating the ethyl acetate solution, recovering ethyl acetate under reduced pressure, and concentrating to give 1.56 kg of a thick paste B for later use; and Step 5: adding the thick paste B obtained in Step 4 to 7.8 kg of methanol, dissolving by heating, filtering while hot, standing and cooling the filtrate for 48 h, crystallizing, filtering to obtain a crystal, and drying the crystal under reduced pressure at a temperature that is not more than 60° C., to obtain 445 g of an extract that is effective in treating drug addiction.

The solvent in Step 2 comprises one of n-hexane, ethanol, methanol, an oil, gasoline, petroleum ether, diethyl ether and ethyl acetate.

The extract is useful in the development of medications and foods for treating drug addiction, and can be prepared into drinks, tablets or capsules.

EXAMPLE 4

An extract that is effective in treating drug addiction is provided, which mainly comprises a cholestenol compound with hydroxyl at position 3 and a double bond between position 5 and position 6, having structural characteristics of

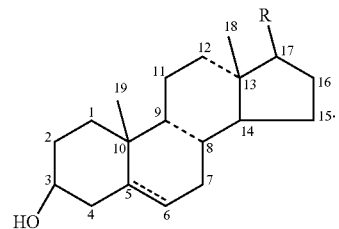

The cholestenol compound comprises β-sitosterol, having a structural characteristic of

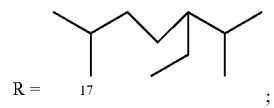

or cholesterol structural characteristic of

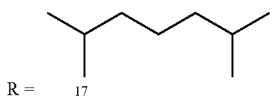

The extract can be extracted from traditional Chinese medicine *Agriolima agrestis*, including one of *Limax maximus* L., *L. flavus* L., *Agriolimax agrestis* L., and *Phiolomycus bilineatus*.

A method for preparing an extract that is effective in treating drug addiction is provided, which comprises the following steps:

Step 1: removing impurities from the traditional Chinese medicine *Agriolima agrestis*, and smashing to 20 meshes for later use;

Step 2: weighing 150 kg of the traditional Chinese medicine *Agriolima agrestis* treated in Step 1, feeding to a multi-functional extractor; adding a mixed solvent of chloroform and methane (chloroform:methane 1:1) and extracting twice under reflux, where the first amount of the solvent added is 1500 kg, the time of extraction under reflux is 1.5 hrs, and an extract A is obtained after filtration; and the second amount of the solvent added is 1200 kg, the time of extraction under reflux is 1.0 hr, and an extract B is obtained after filtration; combining the extract A and the extract B, and recovering the chloroform and methane under reduced pressure, to obtain 18.6 kg of a thick paste A for later use;

Step 3: adding the thick paste A obtained in Step 2 to potassium hydroxide and deionized water, mixing uniformly according to a weight ratio of the thick paste A: potassium hydroxide:deionized water 1:1:1.5, that is, adding 18.6 kg of the thick paste A, 18.6 kg of potassium hydroxide and 27.9 kg of deionized water to a reactor, and heating with stirring to cause a saponification reaction, where the heating temperature is 100° C. and the reaction time is 4 h, to produce a reaction solution that is allowed to stand and cool for later use;

Step 4: adding the reaction solution obtained in Step 3 to an extractor, adding ethyl acetate, and extracting (×4), where the amount of ethyl acetate added is 195.3 kg upon each extraction; washing the formed ethyl acetate solution layer with deionized water (×7), until the washing liquid is neutral (pH=7); separating the ethyl acetate solution, recovering ethyl acetate under reduced pressure, and concentrating to give 2.7 kg of a thick paste B for later use; and Step 5: adding the thick paste B obtained in Step 4 to 13.5 kg of methanol, dissolving by heating, filtering while hot, standing and cooling the filtrate for 48 h, crystallizing, filtering to obtain a crystal, and drying the crystal under reduced pressure at a temperature that is not more than 60° C., to obtain 692 g of an extract that is effective in treating drug addiction.

The extract is useful in the development of medications and foods for treating drug addiction, and can be prepared into drinks, tablets or capsules.

In order to verify the efficacy of *Agriolima agrestis* extract in treating drug addiction, the following experiments are carried out in the present invention:

Experiment 1

50 Sprague-Dawley rats (female:male 1:1) were randomized into 5 groups. Group (1) was a blank control group, and the rats were subcutaneously injected with normal saline. Morphine-dependent rat models were established in the remaining groups (2)-(5) by subcutaneously injecting increasing doses of morphine hydrochloride once every 12 hrs, in which the dose was increased upon each administration from 5 mg/kg gradually to 80 mg/kg, and was continuously administered until the 7th day, the injection volume was 0.2 ml/100 g, and the volume administered in each group was the same. On the 8th day of the experiment, morphine was discontinued and the naloxone-precipitated withdrawal test was performed. Each group was given a different treatment. Group (1), that is, the blank control group, was given the same volume of normal saline. Group (2), that is, the morphine model group, was given the same volume of normal saline. Group (3), that is, the positive control group, was given 20 mg/kg of methadone. Groups (4) and (5), that is, groups with low and high doses of *Agriolima agrestis* extract prepared in the present invention, were given *Agriolima agrestis* extract at a dosage of 0.3 g/kg and 0.6 g/kg respectively. Each group of rats was administered for consecutive 3 days. The rats were allowed to free access to water and food. 45 minutes after administration on the first and third days of treatment, naloxone (5 mg/kg) was given for precipitation respectively. The withdrawal response of the rats within 30 minutes and the changes of body weight before and after precipitation (1 h) were observed. The results are shown in a table below.

TABLE 1

Naloxone-precipitated withdrawal symptom scores in morphine-dependent rats

| | Day 1 | Day 3 |
|---|---|---|
| Blank control group | 4.5 ± 3.88 | 1.4 ± 1.69 |
| Morphine model group | 81.3 ± 32.11 | 44.5 ± 8.09 |
| Positive control group | 49.35 ± 14.41 | 35.6 ± 18.73 |
| Group with low-dose *Agriolima agrestis* extract | 74.9 ± 42.03 | 25.5 ± 12.26 |
| Group with high-dose *Agriolima agrestis* extract | 53.8 ± 16.23 | 22.1 ± 10.90 |

From the data in the table, it can be known that the *Agriolima agrestis* extract can inhibit the precipitated withdrawal symptoms in morphine-dependent rats, and the high-dose group has significantly lower withdrawal symptom scores than the model group.

TABLE 2

Difference in body weight of each group of rats (body weight before precipitation − body weight after precipitation)

| | Day 1 (g) | Day 3 (g) |
|---|---|---|
| Blank control group | 0.5 ± 3.20 | 1.0 ± 1.05 |
| Morphine model group | 10.5 ± 5.48 | 3.6 ± 2.41 |
| Positive control group | 15.6 ± 6.39 | 2.6 ± 2.75 |
| Group with low-dose *Agriolima agrestis* extract | 11.8 ± 3.25 | 4.5 ± 2.59 |
| Group with high-dose *Agriolima agrestis* extract | 14.7 ± 4.08 | 1.9 ± 2.13 |

From the data in the table, it can be known that the two doses of *Agriolima agrestis* extract have no significant effect on the weight loss of the addicted rats.

Experiment 2

50 KM mice (female:male 1:1) were randomized into 5 groups. Group (1) was a blank control group, and the mice were subcutaneously injected with normal saline. Morphine-dependent rat models were established in the remaining groups (2)-(5) by subcutaneously injecting increasing doses of morphine twice daily, once every 12 hrs, in which the dose was increased daily from 25 mg/kg to 160 mg/kg on the 6th day, the injection volume was 0.2 ml/100 g, and the volume administered in each group was the same. On the 7th day of the experiment, morphine was discontinued and the naloxone-precipitated withdrawal test was performed. Each group was given a different treatment. Group (1), that is, the blank control group, was given the same volume of normal saline. Group (2), that is, the morphine model group, was given the same volume of vegetable oil. Group (3), that is, the positive control group, was given 20 mg/kg of methadone. Groups (4) and (5), that is, groups with low and high doses of *Agriolima agrestis* extract prepared in the present invention, were given *Agriolima agrestis* extract at a dosage of 0.4 g/kg and 0.8 g/kg respectively. Each group of mice was administered for consecutive 3 days. The mice were allowed to free access to water and food. 1 hrs after administration on the first and third days of treatment, naloxone (8 mg/kg) was given for precipitation respectively. The jump reaction of the mice in each group within 30 minutes and the changes of body weight before and after precipitation were observed. The results are shown in a table below.

TABLE 3

Jumps of morphine-dependent mice upon precipitated withdrawal

|  | Day 1 (jumps/30 min) | Day 3 (jumps/30 min) |
| --- | --- | --- |
| Blank control group | 0.4 ± 0.699 | 0.5 ± 0.84 |
| Morphine model group | 63.2 ± 14.65 | 12.5 ± 6.09 |
| Positive control group | 25.1 ± 6.9 | 22.9 ± 6.81 |
| Group with low-dose Agriolima agrestis extract | 13.5 ± 10.29 | 6.2 ± 5.86 |
| Group with high-dose Agriolima agrestis extract | 35.0 ± 12.28 | 8.5 ± 2.68 |

From the data in the table, it can be known that the *Agriolima agrestis* extract has a therapeutic effect on precipitated withdrawal symptoms in morphine-dependent mice, and can inhibit the jump reactions of morphine-dependent mice upon precipitated withdrawal.

TABLE 4

Difference in body weight of each group of mice (body weight before precipitation − body weight after precipitation)

|  | Day 1 (g) | Day 3 (g) |
| --- | --- | --- |
| Blank control group | 0.19 ± 0.17 | 0.34 ± 0.31 |
| Morphine model group | 0.53 ± 0.19 | 0.55 ± 0.29 |
| Positive control group | 0.22 ± 0.19 | 0.46 ± 0.23 |
| Group with low-dose Agriolima agrestis extract | 0.18 ± 0.13 | 0.36 ± 0.28 |
| Group with high-dose Agriolima agrestis extract | 0.26 ± 0.21 | 0.43 ± 0.23 |

From the data in the table, it can be known that the *Agriolima agrestis* extract promotes the recovery of weight loss of morphine-dependent mice.

Experiment 3

40 KM mice (female:male 1:1) were fastened for 12 hrs, but allowed to free access to water. The mice were randomly divided into 4 groups, including a blank control group, a group with low-dose *Agriolima agrestis* extract (0.4 g/kg) prepared in the present invention, a group with high-dose *Agriolima agrestis* extract (0.8 g/kg) prepared in the present invention, and a positive control group (estazolam 2 mg/kg). Each group of mice was placed in a YLS-1A multifunctional small animal spontaneous activity recorder. After 5 minutes of accommodation, the number of spontaneous activities of the mice before administration was measured, and the recording time was 10 min. Each group of mice was administered at the above dosage, and the blank control group was administered by oral gavage with the same volume of normal saline. Each mouse was intraperitoneally injected with morphine (10 mg/kg) 30 min after administration. After 15 minutes, the mice were placed in the recorder to observe and record the number of activities of the mice within 10 min. The results are shown in a table below.

TABLE 5

Effect of Agriolima agrestis extract on morphine-induced excitability

|  | Activities before administration (counts/min) | Activities after administration (counts/min) |
| --- | --- | --- |
| Blank control group | 164.1 ± 32.41 | 217.5 ± 23.79 |
| Group with low-dose Agriolima agrestis extract | 191.5 ± 35.53 | 102.0 ± 46.29 |
| Group with high-dose Agriolima agrestis extract | 185.4 ± 36.93 | 112.7 ± 23.04 |
| Positive control group | 171.2 ± 38.94 | 67.9 ± 40.31 |

From the data in the table, it can be known that the *Agriolima agrestis* extract has an inhibitory effect on the morphine-induced excitability in mice.

Experiment 4

40 KM mice (female:male 1:1) were fastened for 12 hrs, but allowed to free access to water. The mice were randomly divided into 4 groups, including a blank control group, a group with low-dose *Agriolima agrestis* extract (0.4 g/kg) prepared in the present invention, a group with high-dose *Agriolima agrestis* extract (0.8 g/kg) prepared in the present invention, and a positive control group (estazolam 2 mg/kg). Each group of mice was placed in a YLS-1A multifunctional small animal spontaneous activity recorder. After 5 minutes of accommodation, the number of spontaneous activities of the mice before administration was measured, and the recording time was 10 min.

Each group of mice was administered by oral gavage at the above dosage, and the blank control group was administered with the same volume of normal saline. Each mouse was intraperitoneally injected with amphetamine (8 mg/kg) 30 min after administration. After 15 minutes, the mice were placed in the recorder to observe and record the number of activities of the mice within 10 min. The results are shown in a table below.

TABLE 6

Effect of Agriolima agrestis extract on amphetamine-induced excitability

|  | Activities before administration (counts/min) | Activities after administration (counts/min) |
| --- | --- | --- |
| Blank control group | 162.3 ± 40.50 | 233.9 ± 56.445 |
| Group with low-dose Agriolima agrestis extract | 192.0 ± 45.06 | 130.6 ± 32.11 |
| Group with high-dose Agriolima agrestis extract | 197.4 ± 39.30 | 132.6 ± 26.26 |
| Positive control group | 183.7 ± 32.99 | 83.0 ± 40.14 |

From the data in the table, it can be known that the *Agriolima agrestis* extract has an inhibitory effect on the amphetamine-induced excitability in mice.

Experiment 5

40 KM mice (female:male 1:1) were fastened for 12 hrs, but allowed to free access to water. The mice were randomly divided into 4 groups, including a blank control group, a group with low-dose *Agriolima agrestis* extract (0.4 g/kg) prepared in the present invention, a group with high-dose

*Agriolima agrestis* extract (0.8 g/kg) prepared in the present invention, and a positive control group (estazolam 2 mg/kg). Each group of mice was administered at the above dosage, and the blank control group was administered with the same volume of normal saline. After 45 minutes, each mouse was given 50 mg/kg of pentobarbital sodium, and then the sleep time of each group of mice was recorded (where the time at which the righting reflex disappeared after the administration was taken as the sleep onset time of the mice, and the duration from the time at which the righting reflex disappeared to the time at which the righting reflex returned was taken as the sleep time). The results are shown in a table below.

TABLE 7

Effect of *Agriolima agrestis* extract on the sleep time with pentobarbital sodium

|  | Sleep time of mice (min) |
| --- | --- |
| Blank control group | 25.8 ± 5.01 |
| Low-dose *Agriolima agrestis* extract group | 39.5 ± 11.46 |
| High-dose *Agriolima agrestis* extract group | 32.8 ± 9.56 |
| Positive control group | 66.22 ± 13.77 |

From the data in the table, it can be seen that the *Agriolima agrestis* extract can prolong the sleep time of mice with a threshold dose of pentobarbital sodium.

Experiment 6

30 Sprague-Dawley rats (female:male 1:1) were randomly divided into 3 groups, including a morphine control group, an *Agriolima agrestis* extract group, and a negative control group, each group having 10 animals. Both the morphine control group and the *Agriolima agrestis* extract group were administered with increasing dose. The morphine control group was injected subcutaneously with morphine hydrochloride twice a day. According to the principle of increasing dose, the dosage of morphine was increased upon each administration from 5 mg/kg to 60 mg/kg, and continuously administered until the 7th day. The Agriolima agrestis extract group was administered twice a day by oral gavage with increasing dose. The dosage was increased daily from 0.5 mg/kg to 3.0 g/kg and continuously administered until the 7th day. The negative control group was given the same volume of vegetable oil daily, and the administration time and frequency were the same as those in the Agriolima agrestis extract group. On the 8th day, rats in each group were given naloxone (5 mg/kg) for precipitation, and the withdrawal state of rats within 30 minutes after precipitated withdrawal and the changes in body weight before and 1 h after withdrawal were observed. The results are shown in a table below.

TABLE 8

Effect of *Agriolima agrestis* extract on the sleep time with pentobarbital sodium

|  | Withdrawal response score | Weight loss (g) |
| --- | --- | --- |
| Negative control group | 2.9 ± 2.24 | 0.2 ± 3.39 |
| Morphine control group | 76.9 ± 14.53 | 9.5 ± 3.62 |
| *Agriolima agrestis* extract group | 7.2 ± 3.37 | 1.1 ± 2.46 |

Weight loss is an important sign of opioid addiction and withdrawal. From the data in the table, it can be known that significant weight loss is accompanied during the precipitated withdrawal of morphine-dependent rats. The animals in the *Agriolima agrestis* extract group show no significant weight loss, indicating that the *Agriolima agrestis* extract does not have physical dependence.

It has been proved by a number of animal experiments that the extract that is effective in treating drug addiction prepared by the present invention has a detoxification treatment effect on the withdrawal symptoms of morphine-dependent rats or mice, and an inhibitory effect on the excitability of mice induced by morphine and benzedrine, and is sedative and hypnotic. The extract is safe in acute toxicity, has no physical or mental dependence, is useful in the development of food and medicines in the future, and can be prepared into drinks, tablets, capsules and the like.

The foregoing is a further detailed description of the present invention in conjunction with specific preferred embodiments, and it should not be considered that the specific implementation of the present invention is limited thereto. Some variations or replacements can be made to the embodiments described herein by those ordinarily skilled in the art to which the present invention pertains without departing from the conception of the present invention, which are all regarded as falling within the protection scope of the present invention.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method for preparing an extract effective in treating drug addiction, comprising following steps:
    S1: removing impurities from *Agriolima agrestis*, and smashing to 20 meshes for later use;
    S2: feeding the *Agriolima agrestis* treated in Step S1 to a supercritical $CO_2$ extractor, and extracting for 4 hrs under a pressure of 25 KPa, at a temperature of 65° C. and a flow rate of 400-500 PV, to produce an extract for later use;
    S3: adding the extract obtained in Step S2 to potassium hydroxide and deionized water, mixing uniformly according to a weight ratio of the extract: potassium hydroxide: deionized water 1:1:1.5, and heating with stirring to cause a saponification reaction, where the heating temperature is 85-100° C. and the reaction time is 2 hrs, to produce a reaction solution A that is allowed to stand and cool for later use;
    S4: adding the reaction solution A obtained in Step S3 to ethyl acetate, and extracting (x4), where the amount of ethyl acetate added is three times the amount of the reaction solution A upon each extraction; washing the formed ethyl acetate solution layer with deionized water (x6-7), until the washing liquid is neutral (pH=7); separating the ethyl acetate solution, recovering ethyl acetate under reduced pressure, and concentrating to give a thick paste A for later use; and
    S5: adding the thick paste A obtained in Step S4 to methanol, where the amount of methanol is 5 times the amount of the thick paste A, dissolving by heating, filtering, standing and cooling for 48 hrs, crystallizing, filtering to obtain a crystal A, and drying the crystal A under reduced pressure at a temperature that is not more than 60° C., to obtain an extract that is effective in treating drug addiction.

2. A method for preparing an extract effective in treating drug addiction, comprising following steps:
- Step 1: removing impurities from *Agriolima agrestis*, and smashing to 20 meshes for later use;
- Step 2: feeding the *Agriolima agrestis* treated in Step 1 to a multi-functional extractor; adding a solvent and extracting twice under reflux, where the first amount of the solvent added is 10 times the weight of the *Agriolima agrestis*, the time of extraction under reflux is 1.5 hrs, and an extract A is obtained after filtration; and the second amount of the solvent added is 8 times the weight of the *Agriolima agrestis*, the time of extraction under reflux is 1.0 hrs, and an extract B is obtained after filtration; combining the extract A and the extract B, and recovering the solvent under reduced pressure, to obtain a thick paste B for later use;
- Step 3: adding the thick paste B obtained in Step 2 to potassium hydroxide and deionized water, mixing uniformly according to a weight ratio of the thick paste B: potassium hydroxide: deionized water 1:1:1.5, and heating with stirring to cause a saponification reaction, where the heating temperature is 85-100° C. and the reaction time is 2-4 h, to produce a reaction solution B that is allowed to stand and cool for later use;
- Step 4: adding the reaction solution B obtained in Step 3 to ethyl acetate, and extracting (x4), where the amount of ethyl acetate added is three times the amount of the reaction solution B upon each extraction; washing the formed ethyl acetate solution layer with deionized water (x6-7), until the washing liquid is neutral (pH=7); separating the ethyl acetate solution, recovering ethyl acetate under reduced pressure, and concentrating to give a thick paste C for later use; and
- Step 5: adding the thick paste C obtained in Step 4 to methanol, where the amount of methanol is 5 times the amount of the thick paste C, dissolving by heating, filtering, standing and cooling for 48 h, crystallizing, filtering to obtain a crystal B, and drying the crystal B under reduced pressure at a temperature that is not more than 60° C., to obtain an extract that is effective in treating drug addiction.

3. The method for preparing an extract effective in treating drug addiction according to claim 2, wherein the solvent in Step 2 comprises one or two of n-hexane, ethanol, methanol, acetone, chloroform, an oil, gasoline, petroleum ether, diethyl ether and ethyl acetate.

* * * * *